United States Patent [19]

McBride et al.

[11] Patent Number: 5,576,198
[45] Date of Patent: Nov. 19, 1996

[54] CONTROLLED EXPRESSION OF TRANSGENIC CONSTRUCTS IN PLANT PLASTIDS

[75] Inventors: Kevin E. McBride; David M. Stalker, both of Davis, Calif.

[73] Assignee: Calgene, Inc., Davis, Calif.

[21] Appl. No.: 167,638

[22] Filed: Dec. 14, 1993

[51] Int. Cl.$^6$ ............................. A01H 4/00; C12N 15/82
[52] U.S. Cl. .................. 435/91.3; 435/240.4; 435/172.3; 800/205
[58] Field of Search ............................. 435/172.3, 240.4, 435/235.1, 320.1, 91.3; 800/205; 536/23.72, 24.1

[56] References Cited

U.S. PATENT DOCUMENTS 5,409,823  4/1995  Crossland et al. .................... 435/172.3

OTHER PUBLICATIONS

Svab, et. al. "High–Frequency Plastid Transformation in Tobacco by Selection for a Chimeric aadA Gene" *Proc. Natl. Acad. Sci, USA* 1993 vol. 90 913–917.
Svab, et. al. "Stable Transformation of Plastids in Higher Plants" *Proc. Natl. Acad. Sci, USA* 1990 vol. 87 8526–8530.
Boynton, et. al. "Chloroplast Transformation in *Chlamydomonas* with High Velocity Microprojectiles" *Science*, 1988 vol. 240: 1534–1538.
Ohyama, et. al. "Chloroplast Gene Organization Deduced from Complete Sequence of Liverwort *Marchantia polymorpha* Chloroplast DNA" *Nature* 1986, vol. 322 572–574.
Hiratsuka, et. al. "The Complete Sequence of the Rice (*Oryza sativa*) Chloroplast Genome: Intermolecular Recombination Between Distinct tRNA Genes Accounts for a Major Plastid DNA Inversion During the Evolution of Cereals" *Mol. Gen. Genet.* 1989 vol. 217 185–194.
Shinozaki, et. al., "The Complete Nucleotide Sequence of the Tobacco Chloroplast Genome: its Gene Organization and Expression" *The EMBO Journal* 1986 vol. 5 No. 9 2043–2049.
Rosenberg, et. al "Vectors for Selective Expression of Cloned DNA's by T7 RNA Polymerase" *Gene* 1987 vol. 56 125–135.
Benton, et. al., "Signal–Mediated Import of Bacteriophage T7 RNA Polymerase into the *Saccharomyces cerevisae* Nucleus and Specific Transcription of Target Genes" *Molecular and Cell Biology* 1990 vol. 10 No. 1 353–360.
Lieber, et. al. "High Level Gene Expression in Mammalian Cells by a Nuclear T7–phage RNA Polymerase" *Nucleic Acids Research* 1989 vol. 7 No. 21 8485–8493.
Lassner, et. al. "Targeting of T7 RNA Polymerase in Tobacco Nuclei Mediated by an SV40 Nuclear Location Signal" *Plant Molecular Biology* 1991 vol. 17 229–234.
Gruissem, et. al "Control Mechanisms of Plastid Gene Expression" *Critical Reviews in Plant Sciences* 1993 vol. 12 1/2 19–55.

De Block, et. al., "Chloroplast Transformation by *Agrobacterium tumefaciens*" *The EMBO Journal* 1985 vol. 4 No. 6 1367–1372.
Boynton, et. al. "Manipulating the Chloroplast Genome of *Chlamydomonas*—Molecular Genetics and Transformation" *Current Research in Photosynthesis* Proceedings of the VIIth International Conference on Photosynthesis, Stockholm, Sweden, Aug. 6–11, 1989 vol. III 12.509–12.516.
Schinkel, et. al. "Mitochondrial RNA Polymerase: Dual Role in Transcription and Replication" *TIG* 1989 vol. 5, No. 5 149–153.
Masters, et. al., "Yeast Mitochondrial RNA is Homologous to Those Encoded by Bacteriophages T3 and T7" *Cell*, Oct. 9, 1987 vol. 51 89–99.
Daniell, et. al. "Transient Foreign Gene Expression of Chloroplasts of Cultured Tobacco Cells After Biolistic Delivery of Chloroplast Vectors" *Proc. Natl. Acad. Sci, USA* 1990 vol. 87 88–92.
McGraw, et. al. "Sequence and Analysis of the Gene for Bacteriophage T3 RNA Polymerase" *Nucleic Acids Research* 1985 vol. 13 No. 18 6753–6767.
Staub, et. al. "Accumulation of D1 Polypeptide in Tobacco Plastids is Regulated via the Untranslated Region of the psbA mRNA" *The EMBO Journal*, 1993 vol. 12 601–606.
Dunn, et. al. "Targeting Bacteriophage T7 RNA Polymerase to the Mammalian Cell Nucleus" *Gene* 1988 vol. 68 259–266.
O'Neal, et. al. "Isolation of Tobacco SSU Genes: Characterization of a Transcriptionally Active Pseudogene" *Nucleic Acids Research* 1987 vol. 15 No. 21 8661–8677.
Jefferson, et al (1987) EMBO Journal 6(13):3901–3907.
Roy, et al (1988) Nucleic Acids Research 16(24):11759–11767.
Cashmore, et al (1985) Bio/Technology 3: 803–808.

*Primary Examiner*—Che S. Chereskin
*Attorney, Agent, or Firm*—Carl J. Schwedler; Donna E. Scherer

[57] ABSTRACT

Novel compositions and methods useful for genetic engineering of plant cells to provide a method of controlling the timing or tissue pattern of expression of foreign DNA sequences inserted into the plant plastid genome are provided in the instant invention. Constructs include those for nuclear transformation which provide for expression of a viral single subunit RNA polymerase in plant cell tissues, and targeting of the expressed polymerase protein into the plant cell plastids. In addition, plastid expression constructs comprising a viral gene promoter region which is specific to the RNA polymerase expressed from the nuclear expression constructs described above, and a DNA sequence of interest to be expressed in the transformed plastid cells are provided. Plant cells and plants comprising the nuclear and/or plastid constructs described herein are of interest. Of particular interest is a method of controlling expression of the inserted plastid gene constructs in a tissue and/or developmental specific manner in plants comprising both the nuclear polymerase construct and the plastid expression constructs.

16 Claims, 2 Drawing Sheets

CONTROLLED EXPRESSION OF TRANSGENIC CONSTRUCTS IN PLANT PLASTIDS

FIELD OF THE INVENTION

This invention relates to the application of genetic engineering techniques to plants. More specifically, the invention relates to uses of nuclear constructs for expression of specific viral RNA polymerases in conjunction with chloroplast expression constructs using promoters recognized by the specific viral polymerases.

BACKGROUND

The plastids of higher plants are an attractive target for genetic engineering. Plant plastids (chloroplasts, amyloplasts, etioplasts, chromoplasts, etc.) are the major biosynthetic centers that in addition to photosynthesis are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression.

DNA sequence and biochemical data reveal a similarity of the plastid organelle's transcriptional and translational machineries and initiation signals to those found in prokaryotic systems. In fact, plastid derived promoter sequences have been reported to direct expression of reporter genes in prokaryotic cells. In addition, plastid genes are often organized into polycistronic operons as they are in prokaryotes.

Despite the apparent similarities between plastids and prokaryotes, there exist fundamental differences in the methods used to control gene expression in plastids and prokaryotes. As opposed to the transcriptional control mechanisms typically observed in prokaryotes, plastid gene expression is controlled predominantly at the level of translation and mRNA stability by trans-acting nuclear encoded proteins.

Previous studies directed to stable transformation of plant chloroplasts have relied on homologous recombination to incorporate desired gene constructs into leaf plastids. In this manner, transgenic plants homoplastic, or near-homoplastic, for a recombinant DNA construct may be obtained. However, a major drawback to genetic engineering for plastid gene expression is the lack of tissue specific and/or developmental regulation mechanisms to control the timing and/or sites of expression of the desired gene products. Since the entire complement of plastid organelles in the transgenic plants are transformed, the integrated construct is expressed in all plastid containing plant tissues.

A mechanism for controlling expression of sequences inserted into plastids would be useful for optimum modification of plastid pathways which occur in particular tissue types, such as the starch and fatty acid biosynthesis pathways in potato tubers or oilseeds, respectively, flower color pathways, fruit ripening related reactions in various fruit plastids, and pathways which can be targeted to produce herbicide resistance in green plant tissues. In addition, unregulated modification of existing plastid metabolism, for example by reducing expression of a native plastid gene using antisense constructs, and/or introduction of new biochemical pathways could result in the inability to obtain viable plants. For example, alteration of certain pathways in vegetative tissues at an early developmental stage, such as would be observed using non-regulated *E. coli* or chloroplast gene promoters, could result in the production of detrimental end products and thus limit the ability to obtain transgenic plants. However, if the gene for a desired biochemical reaction could be programmed for expression only at a particular stage of development, the reaction could be controlled so as to produce the desired product at the desired period, for example when there is sufficient plant biomass to harvest. In this manner, substantial quantities of the desired end product may be obtained.

RELEVANT LITERATURE

Stable transformation of plastids has been reported in the green algae Chlamydomonas (Boynton et al. (1988) Science 240:1534–1538) and most recently in higher plants (Svab et al. (1990) Proc. Natl. Acad. Sci. USA 87:8526–8530; Svab and Maliga (1993) Proc. Natl. Acad. Sci. USA 90:913–917). These methods rely on particle gun delivery of DNA containing a selectable marker and targeting to the plastid genome by homologous recombination.

The complete DNA sequences of the plastid genomes from liverwort (Ohyama et al. (1986) Nature 322:572–574), rice (Hiratsuka et al. (1989) Mol. Gen. Genet. 217:185–194), and tobacco (Shinozaki et al. (1986) EMBO J. 5:2043–2049) have been reported.

Plastid promoters have been reported to direct expression of reporter genes in prokaryotic cells (Gruissem et al. (1993) Critical Reviews in Plant Sciences 12:19–55).

Selective expression of cloned genes in *E. coli* by T7 polymerase has been reported by Rosenberg et al. (Gene (1987) 56:125–135).

Targeting of T7 RNA polymerase to nuclei in tobacco (Lassner et al. (1991) Plant Mol. Biol. 17:229–234), mouse cells (Lieber et al. (1989) Nucl. Acids Res. 17:8485–8493), and *Saccharomyces cerevisiae* (Benton et al. (1990) Mol. Cell. Biol. 10:353–360) has been reported.

SUMMARY OF THE INVENTION

By this invention, constructs useful for genetic engineering of plant cells to provide a method of controlling the timing or tissue pattern of expression of foreign DNA sequences inserted into the plant plastid genome are provided. Constructs for nuclear transformation provide for expression of a viral single subunit RNA polymerase in plant cell tissues, and targeting of the expressed polymerase protein into the plant cell plastids. Nuclear constructs include those which provide for constitutive expression of the viral polymerase in all plant cells and those which provide for expression preferentially in particular plant tissues and/or at particular developmental stages.

DNA sequences, also referred to herein as polynucleotides, for use in plastid transformation contain a plastid expression construct comprising a viral gene promoter region which is specific to the RNA polymerase expressed from the nuclear expression constructs described above, and a DNA sequence of interest to be expressed in the transformed plastid cells. This portion of the polynucleotide for plastid transformation is referred to herein as the "plastid expression construct". The DNA sequence of interest may be a single encoding region in a sense orientation or in the antisense orientation, for example where reduction of expression of a native plastid gene is desired. The DNA sequence of interest may contain a number of consecutive encoding sequences to be expressed as an operon, for example where introduction of a foreign biochemical pathway into plastids is desired. The polynucleotide for plastid transformation will also include a DNA construct providing for expression of a marker in a plant plastid organelle, wherein said marker provides for selection of plant cells comprising a plastid organelle expressing said marker. This plastid construct is also refered to herein as the "plastid selection construct". The polynucleotide for use in plastid transformation will also contain a means of providing for transfer of the expression and selection constructs into the plastid genome. Conveniently, regions of homology to the target plastid genome which flank the constructs to be transferred are included. Other means of transfer to the plastid genome are also considered herein, such as by methods involving the use of transposable elements.

Plant cells and plants comprising the nuclear and/or plastid constructs described herein are also considered in this invention. Such plants or plant cells may be used in plant breeding or transformation methods to provide plant cells having both the nuclear and plastid constructs of this invention. It is recognized that plant cells comprising both the nucleus and plastid expression constructs of this invention will have an altered phenotype as the result of expression of the DNA sequence of interest in the plastid genome under control of the viral promoter region.

In addition, a method of providing for tissue and/or developmental preferential expression in plant plastids, as well as the resultant phenotype alteration, is provided in plant cells comprising both the nuclear polymerase construct and the plastid expression construct of this invention.

DETAILED DESCRIPTION OF THE INVENTION

Figure 1:
FIG. 1 A schematic of a T7 RNA polymerase expression binary construct, pCGN4026, for nuclear transformation is shown. LB, left T-DNA border; RB, right T-DNA border; 35S, CaMV 35S promoter; nptII, neomycin phosphotransferase gene; tml3', tumor morphology 'large' 3' region; d35S, enhanced CaMV 35S promoter; TP, tobacco small subunit 5' untranslated region, chloroplast transit peptide plus intron I and the first 12 amino acids of the mature protein; T7 RNAP, coding region of the phage T7 RNA polymerase gene minus the start codon; nos3', nopaline synthase 3' region.

A nuclear transformation construct of the instant invention includes any sequence of nucleotides which can be inserted into the genome of a plant cell nucleus and provide for expression of a viral single subunit RNA polymerase fused to a transit peptide region capable of providing for transport of the polymerase protein into a plastid organelle. The viral polymerase encoding sequences of this invention are obtained from a group of morphologically similar bacterial viruses which provide for the synthesis of a DNA-dependent RNA polymerase upon infection of their bacterial host. In contrast to other known DNA-dependent RNA polymerases, the polymerases encoded by this class of bacterial viruses consist of a single protein species (of approximate 100 kD molecular weight, and selectively recognize and provide for transcription from a specific promoter sequence. Some well characterized viruses which encode this type of polymerase include the *E. coli* T3 and T7 phages and the SP6 phage of *Salmonella typhimurium*. Encoding sequences for such polymerases have been reported by McGraw et al. (Nucl. Acids Res. (1985) 13:6753–6766) and Kotani et al. (Nucl. Acids Res. (1985) 15:2653–6664). Other members of this class of bacteriophage include Pseudomonas phage gh-1, Klebsiella phage K11, Citrobacter phage ViIII, and Serratia phage IV. Thus, enclonding sequences for related polymerases from any member of this class of phage can be obtained and used in nuclear expression constructs, such as exemplifed herein by constructs comprising a T7 polymerase encoding sequence.

The sequences which encode a transit peptide region to provide for transport of the viral polymerase into plant plastids are preferably obtained from a plant nuclear-encoded plastid protein, such as the small subunit (SSU) of ribulose bisphosphate carboxylase, plant fatty acid biosynthesis related genes including acyl carrier protein (ACP), stearoyl-ACP desaturase, β-ketoacyl-ACP synthase and acyl-ACP thioesterase, or LHCPII genes. The encoding sequence for a transit peptide which provides for transport to plastids may include all or a portion of the encoding sequence for a particular transit peptide, and may also contain portions of the mature protein encoding sequence associated with a particular transit peptide. There are numerous examples in the art of transit peptides which may be used to deliver a target protein into a plastid organelle. The particular transit peptide enclonding sequence used in the instant invention is not critical, as long as delivery to the plastid is obtained. In the examples provided herein a tobacco RuBISCO SSU gene 5' untranslated region plus coding sequences for the chloroplast transit peptide and 12 amino acids of mature SSU (including intron I) are included in a construct to provide for delivery of nuclear expressed T7 polymerase to tobacco plastids. For delivery of a nuclear expressed T7 polymerase to Brassica plastids, a similar construct in which the tobacco SSU intron I region has been deleted may be employed.

The plant promoter which provides for expression of the transit peptide viral polymerase encoding sequences in the plant cell nucleus may provide for constitutive expression in all plant tissues, or may provide for expression preferentially in particular plant tissues and/or at particular stages in plant development. Constitutive promoters may exhibit higher or lower levels of expression in particular plant tissues, but will generally provide for at least some level of expression in all parts of the plant. Examples of plant constitutive promoters include the 19S and 35S promoters from CaMV, and the promoters from the mas, nos and *ocs Agrobacterium* T-DNA genes. For developmental or tissue preferential expression, useful promoters include those from genes expressed preferentially in plant seeds, fruit, tubers, fiber cells, floral tissues and pollen.

Preferential expression in seed plastids is desirable where modification of fatty acid biosynthesis pathways, modification of storage proteins, or introduction of a new pathway in seeds, such as the bacterial polyhydroxybutyrate (PHB) pathway is desired. Examples of plant functional promoters which may be useful for such applications include those from plant storage protein genes or from genes involved in fatty acid biosynthesis in oilseeds. Examples of such promoters include the 5' regulatory regions from such genes as napin Kridl et al. (1991) Seed Sci. Res. 1:209:219), phaseolin, zein, soybean trypsin inhibitor, ACP, stearoyl-ACP desaturase and oleosin. Seed specific gene regulation is discussed in EP 0 255 378 (2/3/88).

Preferential expression in fruit plastids is desirable, for example, where modification of fruit color or flavor development pathways is desired, or where one wishes to alter the carbohydrate content in plant fruits. Examples of plant functional promoters which may be useful for such applications include those from such fruit related genes as polygalacturonase (Bird et al. (1988) Plant Mol. Biol. 11:651–662), the E-8 gene from tomato (Deikman et al. (1988) EMBO J. 7:3315–3320; DellaPenna et al. (1989) Plant Cell 1:53–63), tomato 2A11 (Pear et al. (1989) Plant Mol. Biol. 13:639–651), or ovary specific promoter regions such as described in WO 91/01324 (2/7/91).

Modification to starch synthesis pathways in major starch storage tissues such as potato tubers or corn seeds may also be accomplished by the plastid expression methods described herein. In such cases, promoters from patatin (Twell et al. (1987) Plant Mol. Biol. 9:365–375), zein or plant starch synthase (Visser et al. (1989) Plant Sci. 64:185–192) may be particularly useful for nuclear expression of a viral single subunit RNA polymerase.

Other plant tissues which can be selectively modified by the constructs and methods described herein include plant floral tissues, and such specialized tissues as cotton boll fibers. Promoters which may be used for nuclear expression of a viral polymerase selectively in floral tissues include those from a chalcone synthase gene, such as the CHS gene A from petunia (Koes et al. (1986) Nucl. Acids Res. 14:5229–5239). For floral color modification, expression or antisense control of anthocyanin or flavonoid type pigments in floral tissues is desired. For a review of plant flower color gene manipulation, see van Tunen et al. (in Plant Biotechnology Series, Volume 2 (1990) Developmental Regulation of Plant Gene Expression, D. Grierson ed.). For fiber tissue modification, use of a tomato p7Z gene promoter for expression in cotton fiber tissues is described in copending application 07/998,158 filed 12/29/92. Other promoters useful for expression in cotton fiber cells have also been reported (Crow, et al., Proc. Natl. Acad. Sci. USA (1992) 89:5769–5773). Desirable cotton fiber modifications include, improvement of strength or texture. Examples of genes which may be used for such improvements included PHB biosynthesis genes, cellulose synthase genes (Saxena et al. (1990) Plant Mol. Biol. 15:673–683) and fungal chitin synthase genes (Bowen et al. (Proc. Nat. Acad. Sci. (1992) 89:519–523).

Another example of useful phenotypic modification to cotton fibers is the production of colored cotton, for example having blue or black colored fibers. Methods for nuclear expression of encoding sequences for pigment production in cotton fibers is described in 07/998,158. For example, for melanin production, two protein encoding sequences from Streptomyces (Bernan et al. (1985) Gene 37:101–110) may be used. The mRNAs for the two proteins, the ORF438 product and tyrosinase, are transcribed from a single promoter Streptomyces. By the instant invention, the operon may be adapted for expression from a specific viral promoter region, such as the T7 promoter described herein, and used for plastid transformation. Similarly, two or more gene products may be required for production of indigo in transformed host cells. Where the responsible enzyme is a monooxygenase, as described in unexamined Japanese Patent Application Kokai 2-119777 (Suzuki et al.), two gene products are required. Where the enzyme is a dioxygenase, such as the naphthalene dioxygenase (ND) described in Kurkela et al. (Gene (1988) 73:355–362), three gene products are required. Use of a tryptophanase encoding sequence may also be desired to increase the amount of indole available for conversion to indigo. Sources of tryptophanase gene sequences include *E. coli* (see, for example Deeley et al. (1982) J. Bacteriol. 151:942–951). Thus, the encoding sequences for such proteins may be provided as operons behind a viral promoter specifically recognized by a single subunit viral polymerase and used in plastid expression constructs as described herein.

In a further embodiment, the instant application provides for methods to preferentially modify plastid pathways which are present in green tissues, or which are preferentially present in actively growing plant tissues, such as meristematic regions. In particular, use of light inducible promoters, such as those from SSU or chlorophyll A/B binding protein genes, for expression of a viral polymerase in green tissues is considered. For actively growing plant tissues, a promoter from an EF-1a gene may be used. See, for example, U.S. Pat. No. 5,177,011 (Shewmaker et al.) issued 1/5/93. Such green tissue or meristematic promoters may find use in conjunction with plastid expression constructs for modifications which provide herbicide tolerance, for example to glyphosate, bromoxynil or imidazolinone herbicides using resistance genes such as described in Stalker et al. (J. Biol. Chem. (1985) 260:4724–4728, Stalker et al. (J. Biol. Chem. (1985) 263:6310–6314, and Sathasivan et al. (Nucl. Acids Res. (1990) 18:2188. In addition, the plastids of such tissues are desirable targets for modifications to provide increased photosynthetic capacity or to provide mechanisms for disease and/or stress resistance.

The DNA sequences, or polynucleotides, for use in plastid transformation of this invention will contain a plastid expression construct comprising a viral gene promoter specifically recognized by the RNA polymerase expressed from the nuclear expression constructs described above, and a DNA sequence of interest to be expressed in the transformed plastid cells under the control of the viral promoter. Thus, where the nuclear polymerase expression construct encodes a T7 polymerase, as discussed in the examples which follow, the plastid construct for expression of the DNA sequence of interest will contain a T7 gene promoter region, so that the DNA sequence of interest is only expressed in the presence of the T7 polymerase. Similarly, where a T3, SP6 or other viral polymerase is expressed as the result of a nuclear transformation, the plastid expression construct will utilize a corresponding gene promoter region.

The specific viral promoter regions used in the constructs described herein may also include portions of the 5' untranslated DNA region of the selected viral gene. For example, the 5' untranslated region from gene 10 of phage T7 has been reported to provide for enhanced translation, and is included in the T7 plastid expression constructs described herein. Different or additional 5' untranslated regions from various sources may find use in the plastid constructs for expression of DNA sequences of interest.

The plastid viral promoter expression constructs will generally include a transcription termination region that is recognized by the viral polymerase encoded by the nuclear construct. Typically, a strong transcription termination region is required when using the specific viral promoters of this invention, and it is thus convenient to use the transcription termination region from the same gene as that from which the specific promoter region was obtained. Thus, in the examples described herein, a T7 gene 10 promoter region and the corresponding gene 10 transcription termination region are used in the plastid T7 expression constructs.

It is noted that various other genes in phage T7 also contain promoter sequences specifically recognized by the T7 single subunit polymerase. Notably, gene 10 of T7 is one of six T7 genes which have an identical 24 bp promoter region. Thus, the promoter from any one of these genes, with or without the corresponding 5' untranslated region may be used for plastid expression constructs encompassed by this invention.

The DNA sequence of interest in the plastid viral promoter expression constructs may be an encoding sequence which is oriented for expression of a particular structural gene, such that the protein encoded by the structural gene sequence is produced in the transformed plastid. In addition, the DNA sequence of interest may include a number of individual structural gene encoding regions such that an operon for expression of a number of genes from a single viral promoter region is produced. Thus, it is possible to introduce and express multiple genes from an engineered or synthetic operon or from a pre-existing prokaryotic gene cluster. Such a method would allow large scale and inexpensive production of valuable proteins and fine chemicals in a particular desired plant tissue or a particular stage of development, depending upon the promoter used to drive nuclear expression of the specific viral polymerase. Such an approach is not practical by standard nuclear transformation methods since each gene must be engineered into a monocistron including an encoded transit peptide for plastid uptake and appropriate promoter and terminator signals. As a result, gene expression levels would be expected to vary widely between cistrons, and generation of a number of transgenic plant lines would be required. Ultimately crosses would be required to introduce all of these cistrons into one plant to get expression to the target biochemical pathway.

Alternatively, the DNA sequence of interest in the plastid constuct may be a fragment of an endogenous plastid gene oriented such that an RNA complementary to the endogenous gene mRNA is produced in the transformed plastid. Such antisense constructs may be used to decrease the expression of the target plastid gene.

In order to provide a means of selecting the desired plant cells following plastid transformation, the polynucleotides for plastid transformation will also contain a construct which provides for expression of a marker gene. Expression of the marker gene product allows for selection of plant cells comprising plastid organelles which are expressing the marker protein. In the examples provided herein, a bacterial aadA gene is expressed under the regulatory control of chloroplast 5' promoter and 3' transcription termination regions. The use of such an expression construct for plastid transformation of plant cells has been described by Svab and Maliga (1993, supra). Expression of the aadA gene confers resistance to spectinomycin and streptomycin, and thus allows for the identification of plant cells expressing this marker gene. Selection for the aadA marker gene is based on identification of plant cells which are not bleached by the presence of streptomycin, or more preferably spectinomycin, in the plant growth medium. Other genes which encode a product involved in chloroplast metabolism may also be used as selectable markers. For example, genes which provide resistance to plant herbicides such as glyphosate, bromoxxynil or imidazolinone may find particular use. Such genes have been reported by Stalker et al. (J. Biol. Chem. (1985) 260:4724–4728; glyphosate resistant EPSP), Stalker et al. (J. Biol. Chem. (1985) 263:6310–6314; bromoxynil resistant nitrilase gene), and Sathasivan et al. (Nucl. Acids Res. (1990) 18:2188; AHAS imidazolinone resistance gene).

In the examples described herein, the aadA gene is under the control of a tobacco 16S rRNA promoter, rrn region and a tobacco rps16 3' termination region. Numerous additional promoter regions may also be used to drive expression of the selectable marker gene, including various plastid promoters and bacterial promoters which have been shown to function in plant plastids.

The polynucleotides for use in plastid transformation will also contain a means of providing for stable transfer of the viral promoter expression construct and the selectable marker construct into the plastid genome. Conveniently, regions of homology to the target plastid genome which flank the constructs to be transferred and provide for transfer to the plastid genome by homologous recombination via a double crossover into the genome. Where the regions of homology are present in the inverted repeat regions (IRA and IRB) of the plastid genome, two copies of the transgene are expected per plastid genome. Typically, the regions of homology with the plastid genome will be approximately 1 kb in size. Smaller regions of homology may also be used, for example as little as 100 bp can provide for homologous recombination into the plastid genome. However, the frequency of recombination and thus the frequency of obtaining plants having transformed plastids may decrease with decreasing size of the homology regions. Example of constructs comprising such regions of homology for tobacco plastid transformation are descibed in Svab et.al. (1990 supra) and Svab and Maliga (1993 supra). Regions useful for recombination into tobacco and Brassica plastid genomes are also described in the following examples. Similar homologous recombination and selection constructs may be prepared using plastid DNA from the target plant species.

Other means of transfer to the plastid genome are also considered herein, such as by methods involving the use of transposable elements. For example, the constructs to be transferred into the plastid genome may be flanked by the inverted repeat regions from a transposable marker which functions in plant plastids. A DNA construct which provides for transient expression of the transposase required to tranfer the target DNA into the plastids is also introduced into the chloroplasts. In this manner, a variety of phenotypes may be obtained in plants transformed with the same expression construct depending on positional effects which may result from insertion of the expression constructs into various locations on the plastid genome. Appropriate transposons for use in such plastic transformation methods include bacterial Tn10, bacteriophage Mu and various other known bacterial transposons.

In developing the constructs of the instant invention, the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA which is employed in the regulatory regions, the viral polymerase encoding sequence and/or the DNA sequences of interest for expression in the plastids. Methods for restriction digests, Klenow blunt end treatments, ligations, and the like are well known to those in the art and are described, for example, by Maniatis et al. (in Molecular cloning: a laboratory manual (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation by joining or removing of sequences, linkers, or the like. Normally, the vectors will be capable of replication in at least a relatively high copy number in E. coli. A number of vectors are readily available for cloning, including such vectors as pBR322, pUC series, M13 series, and pBluescript (Strategene; La Jolla, Calif.).

Any one of a number of methods for transforming the nucleus of plant cells with a viral polymerase expression construct may be used in this invention. Methods for plant cell nuclear transformation may include the use of Ti- or Ri-plasmids, microinjection, electroporation, liposome fusion, DNA bombardment or the like.

Where Agrobacterium is used for transformation of plant cell nuclei, a vector may be used which is introduced into the Agrobacterium host for homologous recombination with TDNA or the Ti- on Ri-plasmid present in the Agrobacterium host. Alternatively, binary vectors which provide for tranfer of the construct to plant cells on a plasmid maintained in Agrobacterium independently of the Ti-plasmid may be used. It is desirable to have the construct bordered on one or both sides by T-DNA, particularly having the left and right borders, more particularly the right border. Included with the nuclear expression construct and the T-DNA borders will be one or more markers, which allow for selection of transformed Agrobacterium and transformed plant cells. A number of markers have been developed for use with plant cells, such as resistance to kanamycin, the aminoglycoside G418, hygromycin, or the like. The particular marker employed is not essential to this invention, one or another marker being preferred depending on the particular host and the manner of construction.

The vector is used for introducing the DNA of interest into a plant cell by transformation into an Agrobacterium having vir-genes functional for transferring T-DNA into a plant cell. The Agrobacterium containing the broad host range vector construct is then used to infect plant cells under appropriate conditions for transfer of the desired DNA into the plant host cell under conditions where replication and normal expression will occur. This will also usually include transfer of the marker, so that cells containing the desired DNA may be readily selected.

Methods of plant nuclear transformation and selection which employ a biolistic, or bombardment, method to transfer the target DNA constructs to plant cells may also be used in the instant invention. Such methods are particularly useful in transformation of plant cells which are less susceptible to Agrobacterium-mediated transformation methods. Bombardment tranformation methods are described in Sanford et al. (1991) Technique 3:3–16; Klein et al. (1992) Bio/Technology 10:286–291.

Generally in transformation of plant cells target explants are incubated with the transformed Agrobacterium or bombarded with DNA coated particles. The plant cells are then grown in an appropriate medium to selectively culture those plant cells which have obtained the desired constructs. Once callus forms, shoot formation can be encouraged by employing the appropriate plant hormones in accordance with known methods and the shoots transferred to rooting medium for regeneration of plants. The plants may then be grown and either pollinated with the same transformed strain or different strains. For production of a homozymgous line, self pollination is used.

Stable transformation of tobacco plastid genomes by particle bombardment has been reported (Svab et al. (1990) Proc. Natl. Acad. Sci. USA 87:8526–8530; Svab and Maliga (1993) Proc. Natl. Acad. Sci. USA 90:913–917). The methods described in the above references may be employed to obtain plants transformed with the plastid transformation constructs described herein. Briefly, such methods involve DNA bombardment of a target host explant, preferably from a tissue which is rich in metabolically active plastid organelles, such as green plant tissues including leaves, and cotyledons. The bombarded tissue is then cultured for ~2 days on a cell division promoting media. The plant tissue is then transferred to a selective media containing an inhibitory amount of the particular selective agent, as well as the particular hormones and other substances necessary to obtain regeneration for that particular plant species. For example, in the above publications and the examples provided herein, the selective marker is the bacterial aadA gene and the selective agent is spectinomycin. The aadA gene product allows for continued growth and greening of cells whose chloroplasts comprise the marker gene product. Cells which do not contain the marker gene product are bleached. The bombarded explants will form green shoots in approximately 3–8 weeks. Leaves from these shoots are then subcultured on the same selective media to ensure production and selection of homoplasmic shoots. As an alternative to a second round of shoot formation, the initial selected shoots may be grown to mature plants and segregation relied upon to provide transformed plants homoplastic for the inserted gene construct.

The transformed plants so selected may then be analyzed to determine whether the entire plastid content of the plant has been transformed (homoplastic transformants). Typically, following two rounds of shoot formation and spectinomycin selection, approximately 50% of the transgenic plantlets analyzed are homoplastic as determined by Southern blot analysis of plastid DNA. These plantlets are selected for further cultivation, both for analysis of the transgenic plastid phenotype (where the nuclear viral polymerase expression construct is also present in the plastid transformant), or for use in methods to transform the viral polymerase construct into the nucleus of the transplastomic plants.

As is demonstrated in the examples herein, the inserted plastic gene construct is maternally inherited in all crosses and expression can be achieved by sexual transmission of an active nuclear gene encoding plastid-targeted T7 RNA polymerase. Thus, there are several possible ways to obtain the plant cells of this invention which have both the nuclear viral polymerase expression construct and the plastid expression construct. In one method, a homozygous nuclear transformed plant expressing the polymerase activity is obtained and retransformed by bombardment to transfer the plastid expression construct into the plastid genome. Conversely, a plastid transformed plant may be obtained by bombardment protocols such as described herein and used in nuclear transformation methods, such as by Agrobacterium-mediated transformation or through particle bombardment, to generate transgenic plants having both nuclear and plastid transgenic constructs. In a third method, the transplastomic plants and nuclear transgenic plants may be contained independently using the respective transformation methods, and plants having both nuclear and plastid transgenic constructs prepared by crossing the nuclear transgenic and plastid transgenic plants using plant breeding techniques. In such a cross, the plastid transgenic plant is used as the maternal parent and the nuclear transgenic plant is the paternal parent.

Where transformation and regeneration methods involving such tissues have been adapted for a given plant species, either by Agrobacterium-mediated transformation, bombardment or some other method, the techniques may be modified for use in selection and regeneration methods to produce plastid-transformed plants. For example, the methods described herein for tobacco are readily adaptable to other solanaceous species, such as tomato, petunia and potato. For Brassica, Agrobacterium-mediated transformation and regeneration protocols generally involve the use of hypocotyl tissue, a non-green tissue which might contain a low plastid content. Thus, for Brassica, preferred target tissues include microspore-derived hypocotyl or cotyledonary tissues (which are green and thus contain numerous plastids) or leaf tissue explants. Although the regeneration rates from such tissues may be low, positional effects, such as seen with Agrobacterium-mediated transformation are not expected, and it will not be necessary to screen numerous successfully transformed plants in order to obtain a desired phenotype.

Thus, the constructs and methods described herein may be employed with a wide variety of plant life, depending on the type of pathway to be modified or added to the plant. For example, for starch modification, potato or corn plants may be transformed. For flower color modification, petunia, rose and carnation are target plant hosts. For modification of fruit quality, tomato may be used. For modification of seed oil quality or seed protein content, oilseed crops such as Brassica, soybean, corn, safflower or sunflower may be used.

In the following examples, introduction of a GUS marker under the control of a phage T7 gene 10 promoter into the plastid genome of plants either expressing or not expressing a nuclear encoded/plastid targeted T7 polymerase is described. The ability to manipulate plastid transgene expression via the action of nuclear encoded/plastid targeted T7 RNA polymerase is demonstrated. The plastid-borne reporter gene, GUS, under control of the phage T7 gene 10 promoter and 5' untranslated region, is only expressed when incorporated into a tobacco line containing an active T7 RNA polymerase gene. The results demonstrate that the viral polymerase is successfully introduced into the plant plastid genome and actively transcribes the GUS gene from the T7 gene 10 promoter. In addition, GUS activity is expressed in the presence, but not the absense of T7 polymerase activity, thus demonstrating the specificity of this reaction and the ability to selectively control expression of plastid transgenic constructs by controlling expression of a nuclear transgenic construct encoding a selective viral single subunit RNA polymerase.

The following examples are provided by way of illustration and not by way of limitation.

EXAMPLES

Example 1 Polymerase Expression Constructs

A. CaMV 35S Promoter Construct

The construct pAR3283 (Dunn et al. (1988) Gene 68:259–266) is digested with BglII/EcoRI to remove the SV40 T-antigen nuclear location signal fused to codon 11 of the T7 polymerase gene. A synthetic adapter (top strand: 5'-GATCTGGATCCAACACGATTAA-CATCGCTAAGAACG-3' and bottom strand: 5'-AAT-TCGTTCTTAGCGATGTTAATCGTGTTGGATCCA-3') is introduced, resulting in pCGN4023. The adapter restores the wild type amino terminal coding region of the T7 RNA polymerase gene except that the methionine start codon is replaced by a BamHI restriction site. The BamHI fragment from pCGN4023 is subcloned into BamHI digested pCGN566 (a plasmid related to pUC18 but conferring resistance to chloramphenicol rather that ampicillin) to provide pCGN4024.

Plasmid pCGN2113 (ATCC Deposit Number 40587 made on 3/2/89) containing a double 35S promoter (−941 to −90/−363 to +2) and tml 3' regulatory region, was digested with SacI/EcoRI to remove the tml 3' region. A SacI/EcoRI fragment from pBI101 (Jefferson et al. (1987) EMBO J. 6:3901–3907) containing the nos 3' was introduced in place of the tml 3'. The resulting plasmid, pCGN1575 was then cut with SphI/XbaI, the ends blunted with Klenow and the plasmid re-ligated to create pCGN1577. BglII linkers were added to the EcoRI site following EcoRI digestion and Klenow treatment of pCGN1577. The NcoI sites in the resulting plasmid, pCGN1579, were then removed by digestion with NcoI, Klenow treatment and re-ligation. The new plasmid, pCGN1594, consists of a shortened version of the double 35S promoter (−526 to −90/363 to +2 relative to the transcription start site) and a 260 bp nos 3'.

A DNA fragment harboring the tobacco RuBISCO SSU gene 5' untranslated region plus coding sequences for the chloroplast transit peptide and 12 amino acids of mature SSU (including intron I) is PCR amplified using the top strand primer 5'-CCCAAGCTTAGATCTCATCTTG-GAAGTTTAAAGG-3' and bottom strand primer 5'-GGG-GAGCTCGTCGACGGATCCGTACTTCT-TCTTGTTAATTGG-3' using clone TSSU 3–8 (O'Neal et al. (1987) Nucleic Acids Res. 15:8661–8677) as template. PCR reactions are done in 100 µl volumes using conditions recommended by Perkin-Elmer/Cetus in a PerkinElmer thermal cycler (GeneAmp System 9600) set for 25 cycles of 94° C./30 sec, 55° C./30 sec, and 72° C./30 sec. The resulting fragment is cloned into pBluescriptII SK+ (Stratagene; LaJolla, Calif.) by digestion with HindIII/SacI. Following DNA sequence verification the resulting plasmid, pCGN3669, is digested with BglII/SacI and the SSU sequences cloned into BamHI/SacI digested pCGN1594. The resulting plasmid, pCGN3672, is cut with BamHI and the modified T7 polymerase gene introduced as a BamHI fragment from pCGN4024. A clone, pCGN4025, in which the T7 polymerase gene is oriented such that it reads as a translational fusion with the mature SSU is selected. pCGN4025 is digested with HindIII/BglII and the d35S/chloroplast transit peptide:T7 polymerase/nos 3' expression construct introduced into HindIII/BamHI digested binary vector pCGN1559 (McBride et al. (1990) Plant Mol. Biol. 14:269–276) resulting in pCGN4026 (FIG. 1).

B. Napin Expression Construct

A HindIII/BamHI fragment containing the tobacco SSU 5' untranslated region, leader peptide encoding region and the encoding region for the first 12 amino acids of the mature SSU protein (including the 1st intron) is obtained by digestion of pCGN3669 (described above). The fragment is cloned into the HindIII/BamHI sites of pCGN986 (described below) replacing a CaMV 35S promoter region and resulting in pCGN4095.

pCGN986 contains a cauliflower mosaic virus 35S (CaMV35) promoter and a T-DNA tml 3'-region with multiple restriction sites between them. The T-DNA tml 3'-sequences were subcloned from the pTiA6 Bam19 T-DNA fragment (Thomashow et. al., Cell (1980) 19:729–739) as a BamHI-EcoRI fragment (nucleotides 9062 to 12,823, numbering as in Barker et al. (Plant Mol. Biol. (1982) 2:335–350). The unique SmaI site at nucleotide 11,207 of the Bam19 fragment was changed to a SacI site and the BamHI site was changed to an EcoRI site using linkers. The expression cassette pCGN986 contains a HindIII site followed by the CaMV 35S promoter, two SalI sites, XbaI, BamHI, SmaI, and KpnI sites and the tml 3' region (nucleotides 11207-9023 of the T-DNA) as a SacI/EcoRI fragment.

The intron region in the SSU portion of pCGN4095 is removed using a synthetic oligonucleotide corresponding to the SSU leader peptide/mature protein region bordered by SphI and BamHI sites. The intronless SphI/BamHI fragment is ligated into pCGN4095, replacing the intron containing SphI/BamHI fragment, and resulting in pCGN4096.

The T7 polymerase encoding region from pCGN4024 (described above) is obtained as an approximately 2.2 kb fragment and cloned into pCGN4096, resulting in pCGN4205 containing the encoding region for the SSU leader peptide plus 12 amino acids of SSU mature and the T7 polymerase encoding region in the same translational reading frame.

An approximately 1.7 kb napin promoter region is cloned as a BglII/HindIII fragment from pCGN3223 into a cloning vector providing chloramphenicol resistance resulting in pCGN4212. pCGN3223 is a napin expression cassette containing 1.725 napin 5' and 1.265 napin 3' regulatory sequences in an ampicillin resistant background. The napin 5' and 3' regulatory regions are the same as those present in pCGN1808 (Kridl et al. Seed Science Research (1991) 1:209–219) but are flanked by different restriction site. The regulatory regions in pCGN3223 are flanked by HindIII, NotI and KpnI restriction sites and unique SalI, BglII, PstI, and XhoI cloning sites are located between the 5' and 3' noncoding regions.

The napin 5' regulatory region is moved as a BglII/HindIII fragment from pCGN4212 into BglII/HindIII digested pCGN4205, resulting in pCGN4217 containing the SSU:T7 polymerase encoding construct positioned in a sense expression orientation between the napin 5' and tml 3' regulatory regions. The napin/SSU:T7 polymerase/tml chimeric gene is cloned as a HindIII/PstI partial digest fragment into binary vector plasmids pCGN1559 and pCGN1548 (McBride et al., supra) resulting in pCGN4225 and pCGN4226, respectively.

C. Phaseolin Expression Construct

An 850 bp BglII fragment of the β-phaseolin 5' noncoding region was obtained from p8.8pro (Hoffman et al. (1987) EMBO J. 6:3213–3221) and cloned into pUC9 (Vieira and Messing (1982) Gene 19:259–268) at the BamHI site to yield pTV796. The phaseolin fragment in pTV796 is oriented such that SmaI site of pUC9 is located 3' to the phaseolin promoter. The phaseolin is subcloned from pTV796 as a HindIII/SmaI fragment into a cloning vector providing chloramphenicol resistance. The resulting clone, pCGN4230, is digested with HindIII and BglII, and the ~800 bp fragment containing the phaseolin promoter is cloned into HindIII/BglII digested pCGN4205 (described above) resulting in pCGN4231. pCGN4231 contains the SSU:T7 polymerase encoding construct positioned in a sense expression orientation between phaseolin 5' and tml 3' regulatory regions. The phaseolin/SSU:T7 polymerase/tml chimeric gene is cloned as a HindIII/PstI partial digest fragment into binary vector plasmids pCGN1559 and pCGN1548 (McBride et al., supra) resulting in pCGN4232 and pCGN4233, respectively.

Example 2 Constructs for Transformation and Expression in Plastids

A. GUS Plastid Expression Construct

The phage T7 polymerase gene 10 promoter and entire 5' untranslated region is PCR amplified (PCR conditions as described above) from pET3a (Rosenberg et al. (1987) Gene 56:125–135) using the top strand primer 5'-GGGAAGCTTGCGAAATTAATACGACTCAC-3' and bottom strand primer 5'-CCCCCATGGGTATATCTCCTTCTTAAAG-3'. The resulting PCR reaction product consists of a 24 bp T7 promoter region and 66 bp of the T7 5' untranslated region. The 5' untranslated region includes a stem-loop structure at the very 5' end followed by sequences containing a translational enhancer (Olins et al. (1988) Gene (Amst.) 73:227–235), a strong prokaryotic ribosome-binding site, and the start codon of gene 10. The T7 PCR fragment is digested with HindIII/NcoI and cloned into HindIII/NcoI digested pUC120 to create pCGN4028. pUC120 is an E. coli expression vector based on pUC118 (Vieria and Messing, Methods in Enzymology (1987) 153:3–11) with the lac region inserted in the opposite orientation and an NcoI site at the ATG of the lac peptide (Vieira, J. PhD. Thesis, University of Minnesota, 1988).

To create a 3' regulatory region, a fusion was created between the psbA3' untranslated region (base pairs 533 to 435 of the tobacco chloroplast genome sequence reported by Shinozaki et al. (1986) EMBO J. 5:2043–2049) and the T7 gene 10 terminator region from pET3a by PCR. In a first reaction, the psbA 3' untranslated region is amplified using the top strand primer 5'GGGGAATTCGATCCTGGCCTAGTCTATAAG3' and bottom strand primer 5'GGTTATGCTAGTTATTGCTCAAAGAAAAAAA-GAAAGGAGC3' with Nicotiana tabacum var. 'Xanthi' total DNA as template. Also, the T7 gene 10 terminator is amplified using top strand primer 5'-GCTCCTTTCTTTTTTTCTTTTGAGCAATAAC-TAGCATAACC-3' and bottom strand primer 5'-CCCCTG-CAGCCGGATATAGTTCCTCC-3' with pET3a DNA as template. In an additional PCR reaction, 5 µl of each of the reaction products from the above psbA 3' and T7 terminator reactions are combined into a final 100 µl reaction mix in which a fusion product is amplified using the top strand primer used in the psbA 3' reaction and the bottom strand primer used in the T7 gene 10 terminator reaction. The fusion product is digested with EcoRI and PstI and cloned into EcoRI/PstI digested pBluescriptII KS(-) (Stratagene) resulting in pCGN4027.

Through further manipulation the T7 promoter region (HindIII/NcoI) and psbA3'/T7 terminator (EcoRI/PstI) are combined with an NcoI/EcoRI GUS gene fragment from pKiwi101 (Janssen et al. (1989) Plant Mol. Biol. 14:61–72) in a pBluescriptIIKS(-) backbone (Stratagene) resulting in pCGN4055.

Thus, in pCGN4055, the GUS gene is situated downstream from the E. coli phage T7 gene 10 promoter region (sequences –24 to +66 relative to the transcription start site) such that the start codon for gene 10 is the start codon of GUS. The T7 gene 10 5' untranslated region is retained since it has been reported to be important for translational enhancement in *E. coli*. The 3' region of the GUS gene construct contains the psbA 3' regulatory element shown to be important in stabilizing the mRNA in green tissues (Gruissem et al. (1993) Critical Reviews in Plant Sciences 12:19–55), as well as the strong rho independent phage T7 gene 10 terminator.

B. Plastid Expression Construct for PHB Operon

A construct for plastid expression of an operon containing the genes involved in the polyhydroxybutyrate (PHB) pathway in Brassica is prepared as follows. The PHB operon from *Alcaligenes eutrophus* is obtained by digesting pAeT41 (Peoples et al. (1989) J. Biol. Chem. 264:15298–15303) with SfuI and EcoRI and cloning the approximately 4.2 kb fragment into ClaI/EcoRI digested BluescriptIIKS(−) (Stratagene), resulting in pCGN4077. pCGN4077 is mutagenized to remove the NcoI site in phbB, and the resulting construct is designated pCGN4082. pCGN4077 is also mutagenized to remove the NcoI site in the phbC coding region and to add an NcoI site at the ATG translation initiation codon. The resulting construct is designated pCGN4081. pCGN4081 and pCGN4082 are digested with XhoI and BglII and the XhoI/BglII fragment of pCGN4081 containing the mutagenized phbC coding region is ligated to the XhoI/BglII fragment of pCGN4082 containing the mutagenized phbB region and the cloning vector sequences. The resulting construct, pCGN4086, contains the entire PHB operon with the internal NcoI sites removed and having an added NcoI site at the ATG translational initiation codon. The PHB operon is obtained by digestion of pCGN4086 with EcoRI and XhoI and cloned into EcoRI/XhoI digested pBluescriptIIKS(+), resulting in pCGN4089. pCGN4089 is digested with EcoRI/NdeI to remove the PHB operon 3' untranslated region, and ligated with an EcoRI/NdeI linker adapter to produce pCGN4098. The PHB operon is obtained by digestion of pCGN4098 with EcoRI and NcoI and cloned into EcoRI/NcoI digested pCGN4211, resulting in pCGN4216. pCGN4211 contains the T7/GUS/psbA3':T73' fragment of pCGN4055 (described above) which was transferred as a HindIII/PstI fragment to HindIII/PstI digested pBluescriptII(−) to provide an ampicillin resistant clone. Digestion of pCGN4211 with EcoRI and NcoI drops out the GUS region. Thus, pCGN4216 contains the PHB operon under the control of the T7 gene 10 promoter region and the psbA3':T73' regions.

Figure 2:
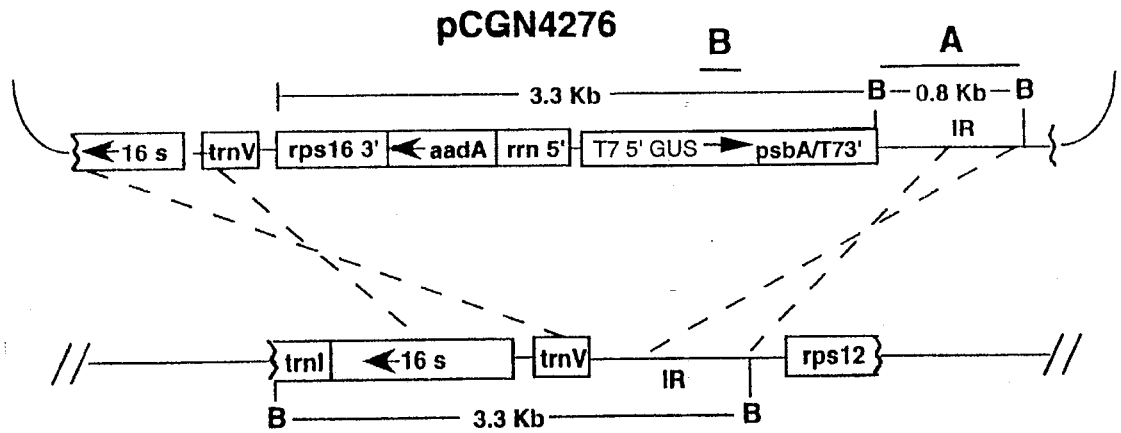
FIG. 2 A construct for preparation of transplastomic tobacco lines containing a T7 RNA polymerase dependent GUS expression marker, and Southern analysis of chloroplast DNA are shown. A schematic of the pCGN4276 construct and representation of incorporation into the tobacco plastid genome are shown at the top. Expected sizes for BamHI fragments are provided for the incoming DNA as well as the wild type DNA. As there is no BamHI site on the 5' end of the incoming DNA, the combined size of the two chimeric genes is indicated. Also shown are the location of probes A and B used for Southern analysis. Probe A determines degree of transformation and probe B reveals presence of the GUS gene. Results of Southern analysis are shown at the bottom of FIG. 2. 4276/4026-3 clones 1 and 2 represent two independent spectinomycin resistant transformants in N. tabacum var. 'Xanthi' line 4026-3. 4276/Xanthi represents a spectinomycin resistant transformant in wild type N. tabacum var. 'Xanthi'. Control DNA is from untransformed 'Xanthi'.
Figure 2:
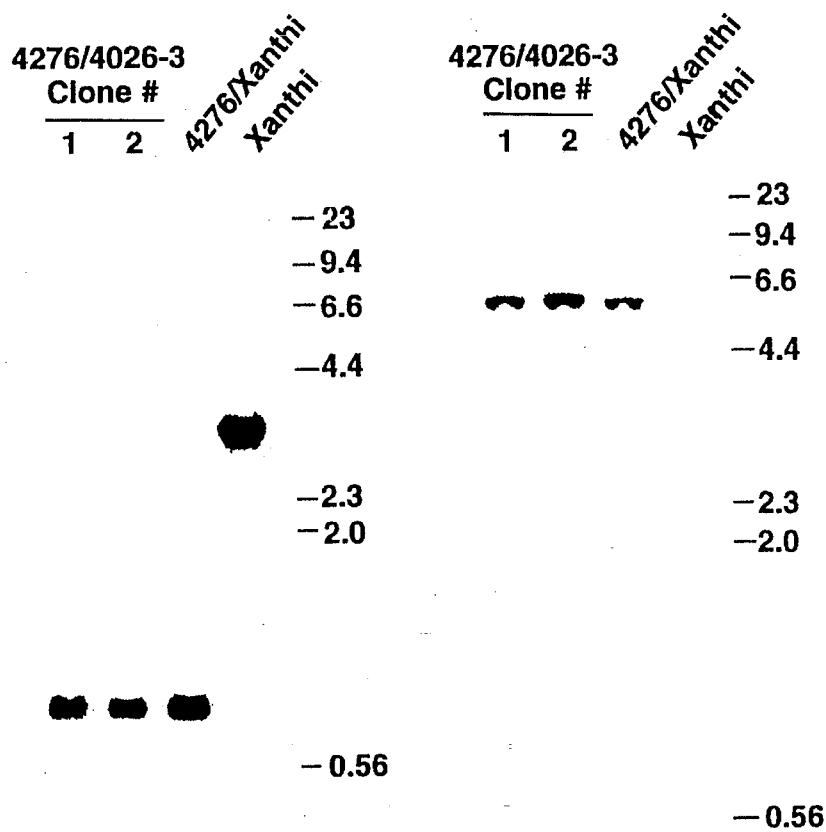

C. Tobacco Transformation Constructs pCGN4055 is digested with HindIII/PstI and the T7 5'/GUS/psbA 3':T7 3' expression construct cloned into a HindIII/PstI digested vector designed for integration of chimeric genes into the tobacco plastid genome by homologous recombination. The resulting construct is designated pCGN4276 (FIG. 2). Bacterial cells comprising the pCGN4276 construct have been deposited at the American Type Culture Collection (ATCC), Rockville, Md. (ATCC#69518). The homologous recombination vector, plasmid OVZ44B, contains a streptomycin/spectinomycin selectable marker gene, aadA, expressed from the tobacco 16S rRNA promoter, rrn (the rrn promoter and aadA regions are described in Svab and Maliga (1993; supra), and having an approximately 150 bp rps16 3' termination region (sequence of the rps16 gene is reported by Shinozaki, K. et al., supra). Similarly, a HindIII/BamHI fragment from pCGN4216 containing the T7/PHB/psbA3':T73' region is transferred as a HindIII/SpeI fragment into HindIII/XbaI digested OVZ44B, resulting in pCGN4295.

The aadA selectable marker construct for plastid transformation is present in OVZ44B on a tobacco chloroplast genome fragment so that it is located just upstream of the trnV locus in the intergenic region between trnV and rps12, and such that at least 1 kb of chloroplast genome DNA borders the aadA expression construct. The plastid DNA bordering fragments provide regions for homologous recombination to occur between the vector and the target plastid DNA sequences. As the homologous recombination site is present in the chloroplast inverted repeat regions (IRA and IRB) (Shinozaki et al., supra), two copies of the transgene are expected per plastid genome (Svab, et al. (1990) supra).

D. Brassica Transformation Construct

In order to obtain a region of homology for recombination into the genome of Brassica plastids, a fragment comprising the rbcL gene which encodes the large subunit of ribulose bisphosphate carboxylase is cloned from Brassica plastid DNA. Plastid DNA may be isolated as described by Doyle et al (Phytochem. Bull. (1987) 19:11–15). Maps of the Brassica napus plastid genome (Warwick et al. (1991) Theor. Appl. Genet. 82:81–92; Palmer et al. (1983) Theor. Appl. Genet. 65:181–189) indicate that the rbcL locus is present on either a 4.3 or 4.8 kb KpnI fragment. To clone this fragment, the plastid DNA is digested with Asp718 (same recognition sequence as KpnI) and cloned into Asp718 digested BluescriptIIKS(−). DNA from resulting clones is analyzed by Southern hybridization using radiolabeled probe containing the rbcL encoding region from tobacco. A clone, pCGN5034, containing an approximately 4.3 kb band which hybridizes to the labeled clone is selected for further localization of the rbcL gene. Following location of the rbcL gene by DNA sequence analysis, appropriate regions for insertion of plastid expression constructs, such as a PHB operon construct as described above, are identified. Desirable regions are those where insertion of the desired gene constructs does not interrupt expression of native plasmid genes, and where the inserted plastid constructs are flanked by regions of homology to provide for homologous recombination by double crossover into the Brassica plastid genome.

Example 3 Agrobacterium-Mediated Nuclear Plant Transformation

Binary constructs for nuclear expression are transformed into cells of an appropriate Agrobacterium strain, such as LBA4404 (Ooms et al. (1982) Plasmid 7:15–29) or EHA101 (Hood et al. (1986) J. Bacteriol. 168:1291–1301) as per the method of Holsters et al. (Mol. Gen. Genet. (1978) 163:181–187) for use in preparation of transgenic plants.

Transgenic tobacco plants are obtained by Agrobacterium-mediated transformation as described by Horsch et al. (Science (1985) 227:1229–1232). Transgenic Brassica plants are obtained by Agrobacterium-mediated transformation as described by Radke et al. (Theor. Appl. Genet. (1988) 75:685–694; Plant Cell Reports (1992) 11:499–505). Transformation of *Gossypium hirsutum* L. cotyledons by co-cultivation with *Agrobacterium tumefaciens* has been described by Firoozabady et al., Plant Mol. Bio. (1987) 10:105–116 and Umbeck et al., Bio/Technology (1987) 5:263–266.

Other plant species may be similarly transformed using related techniques. Alternatively, microprojectile bombardment methods, such as described by Klein et al. (Bio/

Technology 10:286–291) may also be used to obtain nuclear transformed plants comprising the viral single subunit RNA polymerase expression constructs described herein. Cotton transformation by particle bombardment is reported in WO 92/15675, published Sep. 17, 1992.

For example, the binary vector, pCGN4026, harboring a T7 RNA polymerase gene with chloroplast targetting signal sequences is introduced into A. tumefaciens LBA4404 and the resulting Agrobacterium strain used to generate transgenic tobacco lines expressing plastid localized T7 RNA polymerase activity. The chimeric T7 RNA polymerase gene lacking its ATG start codon is expressed from a d35S promoter as a translational fusion to the tobacco small subunit (SSU) transit peptide (TP) and first 12 amino acids of mature SSU. Due to the more or less constitutive nature of the 35S promoter T7 polymerase activity is expected to be expressed in plastids in most all tissues.

Similarly, binary plasmid vectors pCGN4225, pCGN4226, pCGN4232 and pCGN4233 are introduced into A. tumefaciens EHA101 and the resulting Agrobacterium strains used to generate transgenic Brassica plants, such as B. napus var. A112, expressing plastid localized T7 RNA polymerase activity. As the napin and phaseolin promoters providing for expression of the T7 RNA polymerase in these constructs provide for preferential expression in plant seed tissues, T7 polymerase activity is expected to be expressed mainly in the seed tissue plastids.

Example 4 Analysis and Selection of Polymerase Expressing Transgenic Plants

Approximately twenty kanamycin resistant tobacco lines resulting from transformation with pCGN4026 are generated and screened for T7 RNA polymerase activity. T7 RNA polymerase assays are carried out by measuring incorporation of 32P-UTP into pBluescriptII KS(−) transcripts in a reaction containing 40 mM Tris-HCl pH 7.9, 8 mM MgCl2, 5 mM dithiothreitol, 4 mM spermidine-HCl, 0.4 mM each ATP, GTP, CTP, and UTP, and 2 µCi $^{32}$P-UTP. Detectable T7 RNA polymerase activity in the leaf tissue of primary transformants (T1 generation) varied from 0.01 to 2.25 units per µg total protein.

Kanamycin segregation assays are conducted on the seeds of all the positive lines to determine segregation ratios. Three lines, 4026-3, 4026-9, and 4026-11, segregated 3:1 for the resistance gene, indicating that the T7 polymerase construct was inserted at a single chromosomal location. 4026-3, 4026-9, and 4026-11 were self pollinated to create homozygous lines. A T7 RNA polymerase assay on leaves from the homozygous lines demonstrated that 4026-3 had the lowest level of T7 RNA polymerase activity while 4026-9 and 4026-11 had higher levels of polymerase activity. See Table I below.

TABLE 1

T7 Polymerase Activity in Homozygous 4026 Tobacco Lines

| Tobacco Line | Specific Activity (units T7 RNAP*/mg protein) |
|---|---|
| 4026-3 | 0.3 |
| 4026-9 | 1.0 |
| 4026-11 | 0.8 |

*Unit values for T7 RNA polymerase are derived by comparison to a purified enzyme preparation using the assay described above.

Tobacco lines expressing higher levels of plastid-targetted T7 RNA polymerase were observed to have a crinkled leaf morphology. It is possible that excess polymerase is detrimental to the plastids either by providing some level of non-specific transcription or by negatively interacting with the plastid transcriptional complex. If such is the case, addition of a T7 transcriptional unit could further compromise the viability of the plastid organelles. It is noted that the low T7 RNA polymerase producing line, 4026-3, never exhibited a crinkled leaf phenotype until its plastids were transformed with the T7-GUS transcriptional unit (described below).

Example 5 Plant Plastid Transformation Methods

Tobacco plastids are transformed by particle gun delivery of microprojectiles (Svab and Maliga (1993), supra). Since integration into the plastid genome occurs by homologous recombination and the target site is near the ribosomal RNA operon in the inverted repeat, two copies of the transgene are expected per plastid genome (Svab et al. (1990) supra).

Tobacco seeds (N. tabacum v. Xanthi N/C) wildtype and homozygous for pCGN4026 T-DNA are surface sterilized in a 50% chlorox solution (2.5% sodium hypochlorite) for 20 minutes and rinsed 4 times in sterile H$_2$O. The seeds are then plated aseptically on a 0.2 X MS salts media and allowed to germinate. The seedlings are grown on agar solidified MS media with 30 g/l sucrose (Murashige and Skoog (1962) Physiol. Plant 15:493–497).

Tungsten microprojectiles (1.0 µm) are coated with DNA, such as the T7/GUS expression construct, pCGN4276, and the coated microprojectiles used to bombard mature leaves, placed abaxial side up on RMOP media (MS salts, 1 mg/l BAP, 0.1 mg/l NAA, 30 g/l sucrose and 0.7% phytager) (Svab et al. (1990) supra) using the Bio-Rad PDS 1000/He bombardment system (Sanford et al. (1991) Technique 3:3–16; Klein et al. (1992) Bio/Technology 10:286–291). Development of transformed plants on RMOP media supplemented with 500 mg/l spectinomycin dihydrochloride and subsequent subcloning on the same selective medium is conducted according to Svab et al. (1990); Svab and Maliga (1993); supra). Selected plants are rooted in MS media containing 1 mg/l IBA, 500 mg/l spectinomycin dihydrochloride and 0.6% phytagar.

Several homoplasmic non-T7 RNA polymerase producing 'Xanthi' 4276 lines were created in parallel as controls. No fertile transformants were obtained from attempts to transform plastids of the high level T7 RNA polymerase producing line 4026-9 with the pCGN4276 T7/Gus expression construct. A possible explanation for the lack of plastid transformants from 4026-9 is that high level expression of the plastid transgene poses a metabolic drain on the organelle, as has been reported to occur in E. coli when a T7 expression system is used.

Example 6 Analysis of Plants for Expression from a Plastid T7 Promoter Construct Following plastid transformation as described above, two independently isolated homoplasmic lines in the T7 RNA polymerase producing background of 4026-3 were generated and designated as 4026-3 clones 1 and 2. Homoplasmy was demonstrated by Southern blot analysis as shown in FIG. 2. A schematic of pCGN4276 construct and a representation of incorporation into the tobacco plastid genome are shown at the top of FIG. 2. The upper line represents the incoming DNA donated from pCGN4276 and the lower line represents the integration target region. Expected sizes for BamHI fragments are shown for the incoming DNA as well as for wild type DNA. As there is no BamHI site on the 5' end of the incoming DNA the combined size of the two chimeric genes is indicated. Also shown are the location of the two probes, A and B, used for Southern analysis. 4276/4026-3 clones 1 and 2 represent two independent spectinomycin resistant transformants in *N. tabacum* var. 'Xanthi' line 4026-3. 4276/Xanthi represents one spectinomycin resistant transformant in wild type *N. tabacum* var. 'Xanthi'. The control DNA is from untransformed Xanthi. DNA molecular weight markers are in kilobase pairs.

Southern analysis is shown at the bottom of FIG. 2. Total plant cellular DNA is prepared as described by Dellaporta et al. (1983) Plant Mol. Biol. Rep. 1:19–21). Approximately 2 μg DNA for each sample is digested with BamHI, electrophoresed through 1% agarose, transferred to Nytran+ and the filters hybridized with alpha 32P-dCTP labeled probe. Probe A demonstrates degree of transformation (homoplasmy) and probe B reveals presence of the GUS gene. Hybridization with probe A demonstrates that the introduction of a new BamHI site from the transgene changes the size of the probed fragment from 3.3 kb to 0.8 kb in the transplastosomic lines. The degree of homoplasmy is measured by the presence of a residual 3.3 kb band. Only a trace of the wild type 3.3 kb band is observed in the original blots, and the level is not detectable in the reproduction of this blot shown at FIG. 2. It is not apparent if the trace 3.3 kb band represents plastids in which the initial copy of the transgene was not duplicated onto the other inverted repeat, or if a small population of untransformed plastids is present.

To measure T7 RNA polymerase dependent transcription of the GUS gene, total cellular RNA samples from leaf tissue of one clone each of 4276/'Xanthi' and 4276/4026-3 are subjected to Northern analysis with a GUS specific probe. Total plant RNA was prepared as described by Hughes et al. (1988) Plant Mol. Biol. Rep. 6:253–257. A single abundant mRNA band of the expected size (2.1 kb) is present only in the 4276/4026-3 RNA sample. This indicates that transcription of the GUS transgene is dependent on the presence of T7 RNA polymerase. To demonstrate that T7 RNA polymerase does not affect the levels of other transcripts in the two genetic backgrounds a duplicate filter is hybridized with an aadA transgene specific probe and the GUS filter is rehybridized with a psbA specific probe. The results demonstrate that the genetic background has no affect on the relative transcript levels of either the linked aadA transgene or the unlinked psbA gene. Curiously, an aadA-specific transcript of 1.3 kb is present in both lanes in addition to the expected 0.9 kb band. This may be the result of either the aadA transcript not being processed within the boundaries of the rps16 3' or initiation of transcription occurring upstream within the GUS coding region. The intensity of the hybridization signals for each of the mRNAs was quantitated using an Ambis autoradiography scanner and the results indicate that the GUS signal is approximately five-fold higher than the aadA combined signal and five-fold lower than the psbA signal.

To demonstrate that the T7 GUS transcripts are translated in the transgenic plastids, B-glucuronidase specific activity was measured in various tissues. GUS assays are conducted as described by Jefferson et al. (EMBO J. (1987) 6:3901–3907). The results of these assays in various tissues from a 4276/4026-3 clone are shown below in Table 2.

TABLE 2

| B-glucuronidase Activity in Transplastomic Tobacco | | |
|---|---|---|
| 4276 Background | tissue | B-glucuronidase Specific Activity* (nMoles MU/min/mg protein) |
| 4026-3 | leaf | 3000 |
| 4026-3 | stem | 107 |
| 4026-3 | root | 17 |
| 4026-3 | petal | 759 |
| 4026-3 | seed | 4 |
| Xanthi | leaf | 0.14 |
| Xanthi | stem | 0.36 |
| Xanthi | root | 1.2 |
| Xanthi | petal | 0.09 |
| Xanthi | seed | 0.08 |

*MU, fluorescent reaction end product 4-methyl umbelliferone; values based on the average of triplicate tissue samples.

The above results indicate that GUS activity is expressed in all tissues and is highest in leaves and flower petals. Furthermore, expression is dependent on the presence of T7 RNA polymerase since no GUS activity is observed in the xanthi background. By comparison to activity noted in leaf, stem, and petal, GUS activity in developing seed tissue is close to the background level observed for the 4276/Xanthi tissues. The activity seen in root tissue is also low but well above background. GUS activity has also been assayed in leaf and root tissue of a second 4276/4026-3 clone. The same relationship between the level of expression in these two tissues as was observed in the first clone is seen in the leaf and root tissues of the second clone.

The level of GUS mRNA accumulation and β-glucuronidase activity observed in leaf tissue is comparable to levels previously described for tobacco having a psbA5'-GUS-psbA3' plastid transgene (Staub and Maliga (1993) EMBO J. 12:601–606). By comparison of these results, the levels of β-glucuronidase in the above described tobacco plants is estimated to be approximately 1.5–2% of the total soluble protein in these plants. Furthermore, it appears that the level of translational stimulation by the phage mRNA leader is similar to that of the psbAmRNA leader under conditions shown to be optimal for the psbA leader, i.e. fully illuminated leaf tissue (Staub and Maliga, supra). Thus, even with the relatively low level of T7 RNA polymerase activity measured in the 4026-3 transgenic plant, the level of mRNA produced from the plastid T7-transgene is as high as that produced from the psbA promoter, which has been reported to be one of the strongest endogenous plastid promoters (Rapp et al. (1992) J. Biol. Chem. 267:21404–21411).

The lower activity levels in root and developing seed tissue can be explained in part by decreased plastid genome copy number per cell in these tissues. In addition, the psbA3' region in the plastid expression construct has been reported to provide a six-fold increase in mRNA accumulation during light-induced development of photosynthetically active chloroplasts (Deng et al. (1988) EMBO J. 7:3301–3308). Different expression levels of the nuclear-encoded T7 RNA polymerase in various tissues could also be a factor in the β-glucuronidase levels observed. The CaMV 35S promoter which drives expression of the T7 polymerase has been reported to have greater active in leaves and roots than in late developing seeds, the stage at which the above seed samples were analyzed.

In contrast to non-green root and seed tissues, β-glucuronidase accumulation in the upper expanding portion of the flower corolla (post-anthesis) approaches that found in leaf. It has been reported that neither plastid ribosomes nor plastid-specific translational activity can be detected in fully matured chromoplasts of bell pepper fruit and sunflower petals as compared to leaf tissue (Kuntz et al. (1989) Mol. Gen. Genet. 216:156–163). A lack of ribosomes has also been reported in the fully mature daffodil corolla even though roughly 500 chromoplasts are present in each cell (Hansmann et al. (1987) J. Plant Physiol. 131:133–143). Thus, although the translational apparatus may be reduced to a low level in chromoplasts, we are able to detect high levels of expression from the T7/GUS construct in petals, although the levels are 4–5 fold lower than the levels seen in leaves. Messenger RNAs for certain plastid genes, psbA in particular, have been shown to decrease at least 4 to 5-fold in fully mature chromoplasts of bell pepper fruit and sunflower petals (33) as well as in tomato fruit. Furthermore, the lower level of trans-activating T7 RNA polymerase in petal tissue may be explained by reduced activity of the 35S promoter in the expanding portion of the flower corolla. Thus, the lower level of GUS activity compared to the leaf value may be a result of differential mRNA accumulation caused by the psbA3', and/or a decrease in transcriptional or translational activity.

Example 7 Inheritance Studies

To demonstrate that the GUS reporter gene behaves as a maternally inherited character, several crosses were conducted. Seed derived from test and self-crosses were germinated and the seedlings scored for β-glucuronidase activity by staining with the histochemical substrate X-gluc. A self-cross for 4026-3/4276 resulted in 129 positives and no negatives as expected since the nuclear encoded polymerase is homozygous. The wild type nucleus/4276 plastid (female) X 4026-3 nucleus (homozygous)/Xanthi plastid (male) cross resulted in 192 positives and no negatives while for the reciprocal cross there were no positives in 119 seedlings. A cross between homozygous 4026-3/4276 (female) and wild type 'Xanthi' male resulted in 135 out of 135 seedlings tested having a slightly less blue phenotype than the seedlings from the female parent implying a T7 polymerase dosage effect in the heterozygotes. The reverse cross yielded no positives for the 143 seedlings examined. These data confirm that the reporter gene is maternally inherited in all crosses and can be successfully activated by sexual transmission of an active gene encoding plastid-targeted T7 RNA polymerase.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. A method of providing for transcription of a DNA sequence of interest in a plant plastid organelle wherein said method comprises, growing a plant comprising cells, wherein the nuclei of said plant cells comprise a DNA construct comprising the following operably joined components in the 5' to 3' direction of transcription, a promoter functional in said nuclei, an encoding sequence for a plastid transit peptide, an encoding sequence for a viral single subunit RNA polymerase from a member of the T7 class of bacteriophage, and a transcriptional termination region functional in said nuclei, wherein said transit peptide encoding sequence and said RNA polymerase encoding sequences are present in the same translational reading frame, and wherein the genome of said plastid organelle comprises a DNA construct comprising the following operably joined components in the 5' to 3' orientation of transcription, a promoter specific for said viral single subunit RNA polymerase, said DNA sequence of interest, and a transcription termination region.

2. A method according to claim 1, wherein said viral single subunit RNA polymerase is selected from the group consisting of coliphage T7 RNA polymerase, coliphage T3 RNA polymerase, Salmonella phage SP6 RNA polymerase, Pseudomonas phage gh-1 RNA polymerase, Klebsiella phage K11 RNA polymerase, Citrobacter phage ViIII RNA polymerase, and Serratia phage IV RNA polymerase.

3. A method according to claim 1, wherein said promoter functional in said nuclei provides for tissue preferential or developmentally regulated expression.

4. A method according to claim 1, wherein said promoter functional in said nuclei provides for constitutive expression.

5. A plant cell comprising a) a nuclear expression construct comprising as operably joined components in the 5' to 3' direction of transcription a promoter functional in the nucleus of said cell, an encoding sequence for a plastid transit peptide, an encoding sequence for a viral single subunit RNA polymerase from a member of the T7 class of bacteriophage, and a transcriptional termination region functional in said nucleus, wherein said transit peptide encoding sequence and said RNA polymerase encoding sequence are present in the same translational reading frame, and b) a DNA construct in the genome of a plastid organelle of said cell, said DNA construct comprising as operably joined components in the 5' to 3' direction of transcription a promoter specific for said viral single subunit RNA polymerase, a DNA sequence of interest and a transcription termination region.

6. A plant cell according to claim 5 wherein said RNA polymerase is selected from the group consisting of coliphage T7 RNA polymerase, coliphage T3 RNA polymerase, Salmonella phage SP6 RNA polymerase, Pseudomonas phage gh-1 RNA polymerase, Klebsiella phage K11 RNA polymerase, Citrobacter phage ViIII RNA polymerase, and Serratia phage IV RNA polymerase.

7. A plant cell according to claim 5 wherein said promoter functional in a plant cell nucleus provides for constitutive expression.

8. A plant cell according to claim 5 wherein said promoter functional in a plant cell nucleus provides for tissue preferential or developmentally regulated expression.

9. A plant cell according to claim 8 wherein said promoter functional in a plant cell is from a gene which is expressed preferentially in plant seed tissue.

10. A plant cell according to claim 8 wherein said promoter functional in a plant cell is from a gene which is expressed preferentially in a plant starch storage organ.

11. A plant cell according to claim 8 wherein said promoter functional in a plant cell is from a gene which is expressed preferentially in plant floral tissue.

12. A plant cell according to claim 8 wherein said promoter functional in a plant cell is from a gene which is expressed preferentially in plant fruit tissue.

13. A plant cell according to claim 5 wherein said DNA sequence of interest is oriented for transcription of a sequence complementary to an mRNA native to said plastid organelle.

14. A plant cell according to claim 5 wherein said DNA sequence of interest provides for expression of a protein encoding sequence in the sense orientation.

15. A plant cell according to claim 5 wherein said DNA sequence of interest comprises an operon for expression of two or more structural genes.

16. A plant comprising plant cells according to any one of claims 5–15.

* * * * *